(12) United States Patent
Preziosi

(10) Patent No.: US 10,575,914 B1
(45) Date of Patent: Mar. 3, 2020

(54) SURGICAL DRAPE

(71) Applicant: Mark Preziosi, Lakeland, FL (US)

(72) Inventor: Mark Preziosi, Lakeland, FL (US)

( * ) Notice: Subject to any disclaimer, the term of this patent is extended or adjusted under 35 U.S.C. 154(b) by 383 days.

(21) Appl. No.: 15/782,805

(22) Filed: Oct. 12, 2017

(51) Int. Cl.
*A61F 5/37* (2006.01)
*A61B 46/20* (2016.01)
*A61B 46/00* (2016.01)

(52) U.S. Cl.
CPC .............. *A61B 46/20* (2016.02); *A61B 46/40* (2016.02); *A61B 2046/205* (2016.02)

(58) Field of Classification Search
CPC ... A61B 46/20; A61B 46/40; A61B 2046/205; A61B 1/32; A61B 46/00; A61B 46/10; A61B 46/13; A61B 46/17; A61B 46/23; A61B 46/27; A61B 46/30; A61B 2046/234; A61B 2046/236; A61F 5/3769
See application file for complete search history.

(56) References Cited

U.S. PATENT DOCUMENTS

| 7,455,649 B2* | 11/2008 | Root ..................... A61F 5/03 128/849 |
| 7,938,121 B2* | 5/2011 | McKnight ............. A61F 5/3776 128/845 |
| 9,220,627 B2* | 12/2015 | Fisher ..................... A61F 5/03 |
| 2009/0264709 A1* | 10/2009 | Blurton .................. A61B 17/02 600/206 |
| 2017/0156915 A1* | 6/2017 | Choudhury ........... A61F 5/3761 |
| 2017/0165097 A1* | 6/2017 | Patmore ............... A61F 5/3769 |

* cited by examiner

*Primary Examiner* — Anna K Kinsaul
*Assistant Examiner* — Camtu T Nguyen
(74) *Attorney, Agent, or Firm* — Gulf Coast Intellectual Property Group

(57) ABSTRACT

A surgical drape that is configured to have a portion thereof releasably secured to a skin fold and apply a force thereto so as to maintain the skin fold in a biased position away from an incision site. The surgical drape includes a body having a lower portion and an upper portion contiguously formed. The body includes a first side and a second side and further has an adhesive pad secured to the second side of the lower portion of the body. The upper portion of the body includes a first arm member and a second arm member wherein the arm members extend upward towards a patient's head ensuing the surgical drape being superposed a patient. The first arm member and second arm member are oriented to be angularly outward and further define the lateral sides of a void. The void is configured to accommodate a patient torso.

6 Claims, 2 Drawing Sheets

SURGICAL DRAPE

FIELD OF THE INVENTION

The present invention relates generally to medical procedure devices, more specifically but not by way of limitation, a surgical drape particularly designed for obese patients wherein the surgical drape is configured to maintain skin folds away from an incision site.

BACKGROUND

Surgical and medical procedures require that sterile field be present in order to avoid infections. A common device that is deployed during a surgical or medical procedure is a surgical drape. Conventional surgical drapes are employed to keep a surgical site sterile from any adjacent non-sterile surfaces and the surroundings so as to attempt to reduce the infection potential to a patient. Commonly used surgical drapes are typically manufactured sterile so as to aid in the prevention of infection. Conventional surgical drapes are manufactured from a sterile cloth and are typically draped over a desired portion of the body adjacent to and surrounding the surgical site such as but not limited to an incision site.

One issue with conventional surgical drapes is their inability to be secured to a body surface and/or portion and hold the surface or portion in a desired position. A typical surgical drape is superposed a desired location but is unable to accommodate features such as but not limited to skin folds that may propagate into an incision site during a medical procedure. For large obese patients skin folds can be in areas where an incision site must be made and present a challenge to manage during the surgical procedure. Movement of these skin folds during a procedure presents various risks and complications for the surgeon and the patient.

Accordingly, there is a need for a surgical drape that is configured to releasably secure to a patient and in particular a skin fold wherein the surgical drape is configured to maintain the skin fold in a biased position away from an incision site.

SUMMARY OF THE INVENTION

It is the object of the present invention to provide a surgical drape that is configured to maintain a skin fold in a biased position away from an incision site that includes a body manufactured from sterile cloth that is planar in manner.

Another object of the present invention is to provide a surgical drape operable to provide a sterile field adjacent to a surgical area wherein the body has a first side and a second side.

A further object of the present invention is to provide a surgical drape that is configured to maintain a skin fold in a biased position away from an incision site wherein the body includes lower portion and an upper portion that are contiguous.

Still another object of the present invention is to provide a surgical drape operable to provide a sterile field adjacent to a surgical area wherein the upper portion includes a first arm and a second arm.

An additional object of the present invention is to provide a surgical drape that is configured to maintain a skin fold in a biased position away from an incision site wherein a void is present intermediate the first arm and second arm of the upper portion of the body so as to accommodate a torso of a patient.

Yet a further object of the present invention is to provide a surgical drape operable to provide a sterile field adjacent to a surgical area wherein the lower portion of the body includes an adhesive pad on the second side thereof.

Another object of the present invention is to provide a surgical drape that is configured to maintain a skin fold in a biased position away from an incision site wherein the adhesive pad on the second side of the body extends the width of the lower portion and is configured to releasably secure to a skin fold.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
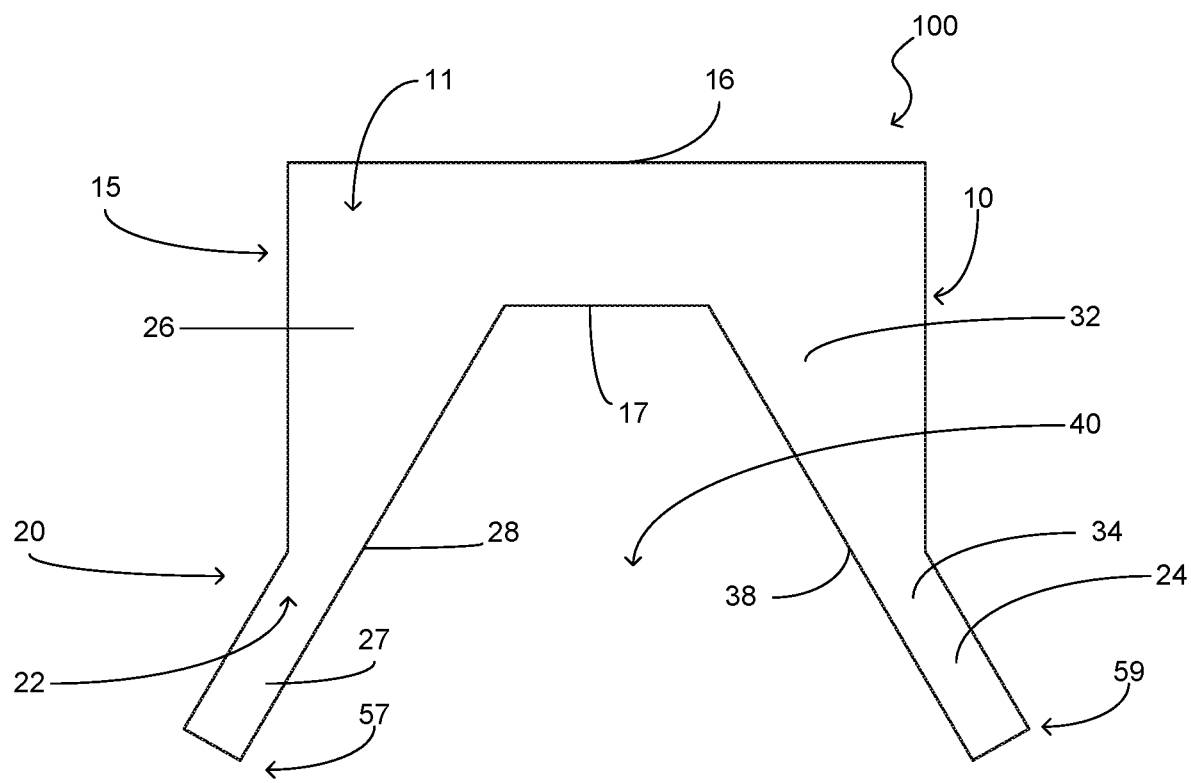
FIG. 1 is a top view of an embodiment of the present invention.

Referring now to the drawings submitted herewith, wherein various elements depicted therein are not necessarily drawn to scale and wherein through the views and figures like elements are referenced with identical reference numerals, there is illustrated a surgical drape 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Figure 2:
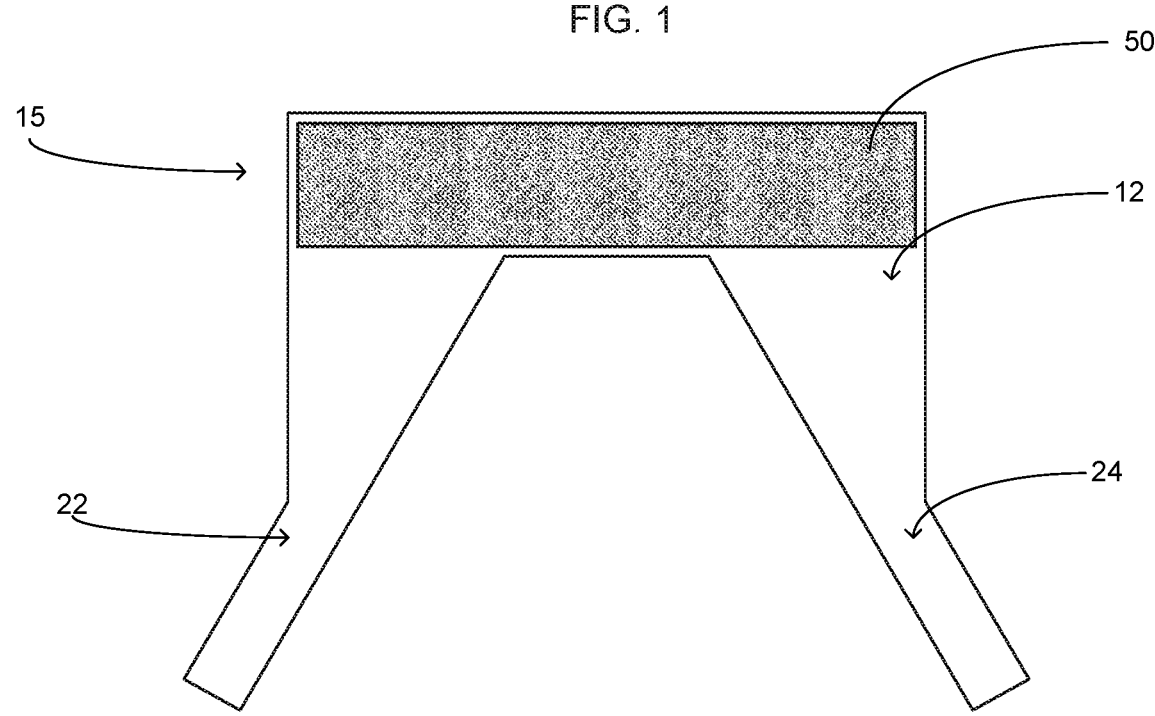
FIG. 2 is a bottom view of an embodiment of the present invention.

Referring in particular to FIG. 1 and FIG. 2 herein the surgical drape 100 includes body 10 that is planar in manner and manufactured from a flexible sterile material. It is contemplated within the scope of the present invention that the body 10 could be manufactured from various different materials and further could be constructed so as to either be disposable or reusable with the proper sterile treating. The body 10 includes a first side 11 and a second side 12. Ensuing being superposed a patient, the first side 11 of the body 10 is distal to the patient and the second side 12 is adjacent to the patient.

The body 10 includes a lower portion 15 and an upper portion 20 that are contiguously formed. The lower portion 15 of the body 10 is generally rectangular in shape and includes lower perimeter edge 16 that extends the width of the lower portion 15 of the body 10. It is contemplated within the scope of the present invention that the body 10 is manufactured having a width that is suitable to accommodate a the torso area of a large human being. The lower portion 15 includes upper edge 17, which is configured to define the void 40 that is further discussed herein.

The upper portion 20 of the body 10 includes a first arm member 22 and a second arm member 24 wherein the first arm member 22 and second arm member 24 are located on opposing sides of the body 10. The first arm member 22 includes a lower section 26 and an upper section 27 contiguously formed wherein the upper section 27 is outwardly angular in manner with respect to the lower portion 26 creating the left inner perimeter edge 28 which assists in defining the void 40 as will be further discussed herein. The second arm member 24 is constructed similarly to the first arm member 22. The second arm member 24 includes a lower section 32 and an upper section 34 that are contiguously formed wherein the upper section 34 is outwardly angular with respect to the lower section 32. The outwardly angular arrangement of the first arm member 22 and second arm member 24 create the void 40. Defining the void 40 are the left inner perimeter edge 28, the right inner perimeter edge 38 and the upper edge 17. The void 40 is configured to accommodate a human torso. In a desired application, the lower portion 15 of the body 10 is secured to a patient abdomen and the first arm member 22 and second arm member 24 extend upward towards the head of the patient. The void 40 accommodates the torso of the patient as shown herein in FIG. 3.

Secured to the second side 12 of the lower portion 15 is adhesive pad 50. The adhesive pad 50 is secured to the second side utilizing suitable durable techniques. The adhesive pad 50 is configured to be releasably secured to a portion of the patient such as but not limited to a skin fold and maintain in a biased position away from an incision site. It is contemplated within the scope of the present invention that various suitable adhesives could be utilized on the adhesive pad 50 to achieve the desired objective. The adhesive pad 50 is sized so as to substantially cover the second side 12 of the lower portion 15 in order to ensure the ability to engage a skin fold that extends the width of the abdomen of the user. While the adhesive pad 50 is illustrated and discussed herein as substantially covering the second side 12 of the lower portion 15, it is contemplated within the scope of the present invention that the size of the adhesive pad 50 could be altered and further additional quantities thereof could be provided in order to accomplish the desired objective stated herein.

Figure 3:
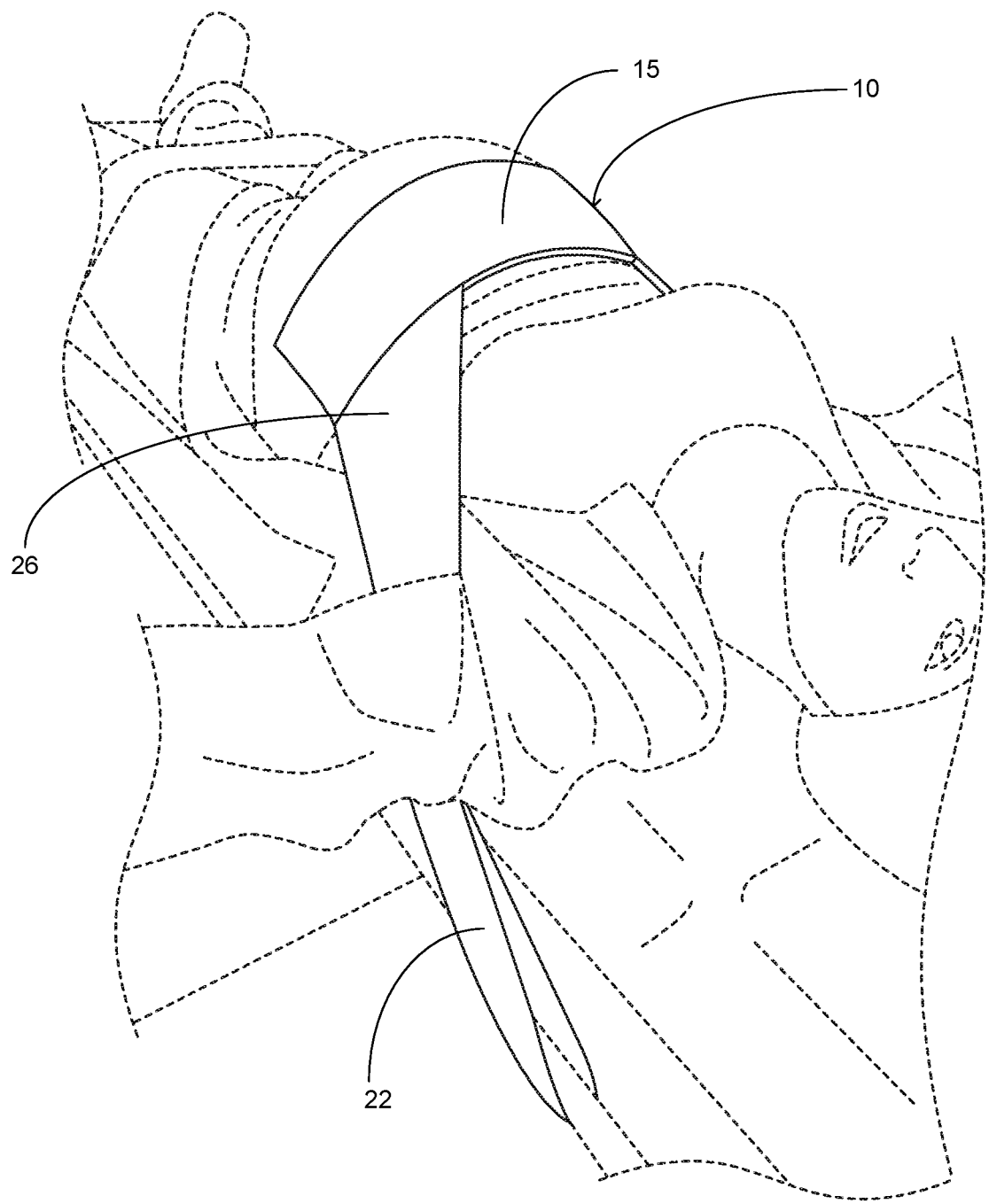
FIG. 3 is a perspective view of the present invention in use.

FIG. 3 herein illustrates the surgical drape 100 in use. Subsequent being superposed a patient the adhesive pad 50 is secured to the abdomen of the patient and in particular a skin fold thereof that needs to be maintained in a biased position away from an incision site. The adhesive pad 50 is secured to a skin fold and the first arm member 22 is passed under the left arm of the patient and the second arm member 24 is passed under the right arm of the patient. The first arm member 22 and second arm member 24 are of suitable length to have the ends 57,59 thereof secured to the table on which the patient is superposed. During the process of securing the first arm member 22 and second arm member 24 sufficient tension is applied thereto in order to employ adequate force so as to move the skin fold to which the adhesive pad 50 is secured so as to maintain the skin fold in a biased position away from an incision site. It is contemplated within the scope of the present invention that the first arm member 22 and second arm member 24 could be configured with fasteners such as but not limited to hook and loop fasteners in order to facilitate the securing thereof to a table. Those skilled in the art should recognize that numerous techniques and elements could be incorporated in the first arm member 22 and second arm member 24 so as to accomplish the ability to secure to a table and apply a force to the lower portion 15.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A surgical drape configured to have a portion thereof releasably secured to a portion of a patient comprising:

a body, said body being planar in manner, said body having a first side and a second side, said body configured to be superposed a patient, said body having a lower portion and an upper portion, said lower portion and said upper portion of said body being contiguously formed, said upper portion of said body having a first arm member and a second arm member, said first arm member and said second arm member being located on opposing sides of the body, wherein said first arm member includes a lower section and an upper section wherein the upper section of the first arm member is oriented in an angularly outward position with respect to the lower section of the first arm member and wherein the upper section of the second arm member is oriented in an angularly outward position with respect to the lower section of the second arm member, said lower section and said upper section being contiguously formed, said lower section of said first arm member being contiguous with said lower portion of said body and wherein said second arm member includes a lower section and an upper section, said lower section and said upper section being contiguously formed, said lower section of said second arm member being contiguous with said lower portion of said body;

a void, said void being intermediate said first arm member and said second arm member, said void configured to accommodate a torso of a patient;

an adhesive pad, said adhesive pad being secured to said lower portion of said body, said adhesive pad being located on said second side of said body, said adhesive pad configured to be releasably secured to a portion of a patient; and wherein the first arm member and second arm member are configured to be secured to a table so as to employ a force on said lower portion of said body in order to maintain the portion of the patient in a biased position away from an incision site.

2. The surgical drape as recited in claim 1, wherein the portion of the patient to which the adhesive pad is secured is a skin fold.

3. A surgical drape configured to have a portion thereof releasably secured to a skin fold of a patient so as to maintain the skin fold in a biased position away from an incision site comprising:

a body, said body being planar in manner, said body having a first side and a second side, said body configured to be superposed a patient, said body having a lower portion and an upper portion, said lower portion and said upper portion of said body being contiguously formed, said upper portion of said body having a first arm member and a second arm member, said first arm member and said second arm member being located on opposing sides of the body, wherein said first arm member includes a lower section and an upper section, said lower section and said upper section being contiguously formed, wherein the upper section of the first arm member is oriented in an angularly outward position with respect to the lower section of the first arm member, said lower section of said first arm member being contiguous with said lower portion of said body and wherein said second arm member includes a lower section and an upper section, said lower section and said upper section being contiguously formed, wherein the upper section of the second arm member is oriented in an angularly outward position with respect to the lower section of the second arm member, said lower section of said second arm member being contiguous with said lower portion of said body, wherein said lower portion of said body further includes an upper edge, said first arm member including a left inner perimeter edge, said second arm member having a right inner perimeter edge, said upper edge of said lower portion being contiguous with said left inner perimeter edge and said right inner perimeter edge so as to define a void, said void being configured to accommodate a patient torso;

an adhesive pad, said adhesive pad being secured to said lower portion of said body, said adhesive pad being located on said second side of said body, said adhesive pad configured to be releasably secured to a portion of a patient, said adhesive pad configure to substantially cover the lower portion of said body; and wherein the first arm member and second arm member are configured to be secured to a table so as to employ a force on said lower portion of said body in order to maintain the skin fold of the patient in a biased position away from an incision site.

4. The surgical drape as recited in claim 3, wherein the first arm member and second arm member include ends, said ends being configured to be secured to a table.

5. A surgical drape configured to have a portion thereof releasably secured to a skin fold of a patient so as to maintain the skin fold in a biased position away from an incision site comprising:

a body, said body being planar in manner, said body having a first side and a second side, said body configured to be superposed a patient, said body having a lower portion and an upper portion, said lower portion and said upper portion of said body being contiguously formed, said upper portion of said body having a first arm member and a second arm member, said first arm member and said second arm member being located on opposing sides of the body, wherein said first arm member includes a lower section and an upper section, wherein the upper section of the first arm member is oriented in an angularly outward position with respect to the lower section of the first arm member, said lower section and said upper section being contiguously formed, said lower section of said first arm member being contiguous with said lower portion of said body and wherein said second arm member includes a lower section and an upper section, said lower section and said upper section being contiguously formed, wherein the upper section of the second arm member is oriented in an angularly outward position with respect to the lower section of the second arm member, said lower section of said second arm member being contiguous with said lower portion of said body;

a void, said void being intermediate said first arm member and said second arm member, said void configured to accommodate a torso of a patient;

an adhesive pad, said adhesive pad being secured to said lower portion of said body, said adhesive pad being located on said second side of said body, said adhesive pad configured to be releasably secured to a portion of a patient; and wherein the first arm member and second arm member are configured to be secured to a table so as to employ a force on said lower portion of said body in order to maintain the skin fold of the patient in a biased position away from an incision site.

6. The surgical drape as recited in claim 5, wherein said adhesive pad substantially covers the lower portion of said body.

* * * * *